(12) United States Patent
Jamison et al.

(10) Patent No.: US 9,134,291 B2
(45) Date of Patent: Sep. 15, 2015

(54) SYSTEMS, METHODS AND DEVICES FOR ANALYZING DRILLING FLUID

(75) Inventors: Dale E. Jamison, Humble, TX (US);
Robert J. Murphy, Kingwood, TX (US); Shawn Broussard, Houston, TX (US); Peter Gonzalez, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 647 days.

(21) Appl. No.: 13/358,872

(22) Filed: Jan. 26, 2012

(65) Prior Publication Data

US 2013/0192360 A1    Aug. 1, 2013

(51) Int. Cl.
*E21B 47/10*    (2012.01)
*G01N 33/28*    (2006.01)
*E21B 21/00*    (2006.01)

(52) U.S. Cl.
CPC ............ *G01N 33/2823* (2013.01); *E21B 21/00* (2013.01)

(58) Field of Classification Search
USPC ................. 73/54.02, 152.19–152.28, 152.54, 73/152.05, 152.18, 152.01, 152.39, 73/152.03, 152.55, 152.46, 152.08; 166/368, 91.1, 95.1, 97.1, 264, 357, 166/267, 316, 336, 75.11, 97.5
See application file for complete search history.

(56) References Cited

U.S. PATENT DOCUMENTS

| 4,557,142 A * | 12/1985 | Hensley et al. ............ 73/152.19 |
| 4,748,849 A | 6/1988 | Jamison et al. ................ 73/61.4 |
| 4,860,580 A * | 8/1989 | DuRocher .................. 73/152.26 |
| 4,900,159 A | 2/1990 | Jamison ........................ 366/343 |
| 5,509,303 A * | 4/1996 | Georgi ........................ 73/152.18 |
| 5,819,853 A * | 10/1998 | Patel ............................. 166/373 |
| 5,845,711 A | 12/1998 | Connell et al. ................ 166/384 |
| 6,474,143 B1 | 11/2002 | Herod .......................... 73/54.01 |
| 6,543,276 B2 | 4/2003 | Murphy, Jr. et al. ......... 73/61.63 |
| 6,584,833 B1 | 7/2003 | Jamison et al. .............. 73/61.63 |
| 6,604,852 B1 | 8/2003 | Murphy, Jr. et al. ........... 374/20 |
| 6,906,535 B2 | 6/2005 | Murphy, Jr. et al. .......... 324/713 |

(Continued)

FOREIGN PATENT DOCUMENTS

| EP | 0211112 | 2/1987 | ............. E21B 21/08 |
| GB | 2479450 A | 10/2011 | |

OTHER PUBLICATIONS

"Chapter F-4, Drilling Fluids," EM 1110-1-1804, Jan. 1, 2001, XP055060505, pp. F-4-1 to F-4-21.

(Continued)

*Primary Examiner* — Hezron E Williams
*Assistant Examiner* — Hoang Nguyen

(57) ABSTRACT

System, methods and devices for analyzing drilling fluids are presented herein. A fluid analysis system for determining at least one characteristic of a drilling fluid is disclosed. The system includes a pump and two reversible fluid ports each configured, when in a first state, to intake drilling fluid into the fluid analysis system and, when in a second state, to expel drilling fluid from the fluid analysis system. A valve fluidly couples the reversible fluid ports to the pump. The valve controls the respective states of the reversible fluid ports. At least one measurement module is fluidly coupled to the pump to receive drilling fluid therefrom. The at least one measurement module is configured to determine at least one characteristic of the drilling fluid. Filters can be fluidly coupled with each of the reversible fluid ports. The filters prevent solids of a predetermined size from entering the fluid analysis system.

20 Claims, 4 Drawing Sheets

(56) References Cited

U.S. PATENT DOCUMENTS

| | | | |
|---|---|---|---|
| 6,981,850 B1* | 1/2006 | Maltbie et al. | 417/201 |
| 7,360,611 B2* | 4/2008 | Sims et al. | 175/206 |
| 7,462,580 B2 | 12/2008 | Kirsner et al. | 507/138 |
| 7,534,743 B2 | 5/2009 | Kirsner et al. | 507/103 |
| 7,581,435 B2* | 9/2009 | Pelletier | 73/54.02 |
| 7,701,229 B2 | 4/2010 | Murphy et al. | 324/698 |
| 7,721,594 B2 | 5/2010 | Rogers et al. | 73/152.02 |
| 7,721,595 B2 | 5/2010 | Rogers et al. | 73/152.02 |
| 7,721,596 B2 | 5/2010 | Rogers et al. | 73/152.02 |
| 7,721,612 B2 | 5/2010 | Jamison | 73/863.23 |
| 7,830,161 B2 | 11/2010 | Murphy | 324/698 |
| 8,622,138 B2* | 1/2014 | Donald et al. | 166/344 |
| 2004/0195007 A1* | 10/2004 | Eppink | 175/61 |
| 2005/0236050 A1* | 10/2005 | Manson et al. | 137/625.11 |
| 2006/0070426 A1* | 4/2006 | Pelletier | 73/54.02 |
| 2006/0254775 A1 | 11/2006 | Jamison | 166/305.1 |
| 2007/0240875 A1* | 10/2007 | Van Riet | 166/91.1 |
| 2008/0066537 A1* | 3/2008 | Hegeman et al. | 73/152.28 |
| 2010/0139387 A1 | 6/2010 | Jamison et al. | 73/152.25 |
| 2010/0283492 A1 | 11/2010 | Growcock et al. | 324/724 |
| 2011/0000713 A1 | 1/2011 | Meeten et al. | |
| 2011/0167901 A1 | 7/2011 | Jamison et al. | 73/152.18 |
| 2011/0203845 A1 | 8/2011 | Jamison et al. | 175/40 |

OTHER PUBLICATIONS

Foreign communication from a related counterpart application—International Search Report and Written Opinion, PCT/US2013/020559, May 7, 2013, 9 pages.

* cited by examiner

SYSTEMS, METHODS AND DEVICES FOR ANALYZING DRILLING FLUID

TECHNICAL FIELD

The present disclosure relates generally to the drilling of boreholes, for example, during hydrocarbon exploration and excavation. More particularly, the present disclosure relates to systems, methods and devices for monitoring and analyzing drilling fluid.

BACKGROUND

Boreholes, which are also commonly referred to as "wellbores" and "drill holes," are created for a variety of purposes, including exploratory drilling for locating underground deposits of different natural resources, mining operations for extracting such deposits, and construction projects for installing underground utilities. A common misconception is that all boreholes are vertically aligned with the drilling rig; however, many applications require the drilling of boreholes with vertically deviated and horizontal geometries. A well-known technique employed for drilling horizontal, vertically deviated, and other complex boreholes is directional drilling. Directional drilling is generally typified as a process of boring a hole which is characterized in that the course of the borehole in the earth is in a direction other than vertical—i.e., the axes make an angle with the vertical plane (known as "vertical deviation"), and are directed in the azimuth plane.

Conventional directional boring techniques traditionally operate from a boring device that pushes or steers a series of connected drill pipes with a directable drill bit at the distal end thereof to achieve the borehole geometry. In the exploration and recovery of subsurface hydrocarbon deposits, such as petroleum and natural gas, the directional borehole is typically drilled with a rotatable drill bit that is attached to one end of a bottom hole assembly or "BHA." A steerable BHA can include, for example, a positive displacement motor (PDM) or "mud motor," drill collars, reamers, shocks, and under-reaming tools to enlarge the wellbore. A stabilizer may be attached to the BHA to control the bending of the BHA to direct the bit in the desired direction (inclination and azimuth). The BHA, in turn, is attached to the bottom of a tubing assembly, often comprising jointed pipe or relatively flexible "spoolable" tubing, also known as "coiled tubing." This directional drilling system—i.e., the operatively interconnected tubing, drill bit and BHA, is usually referred to as a "drill string." When jointed pipe is utilized in the drill string, the drill bit can be rotated by rotating the jointed pipe from the surface, or through the operation of the mud motor contained in the BHA. In contrast, drill strings which employ coiled tubing generally rotate the drill bit via the mud motor in the BHA.

Drilling fluid is often used to aid the drilling of boreholes into the earth, for example, to remove cuttings from the borehole, control formation pressure, and cool, lubricate and support the bit and drilling assembly. Typically, the drilling fluid, which is more commonly referred to as "mud," is pumped down the borehole through the interior of the drill string, out through nozzles in the end of the bit, and then upwardly in the annulus between the drill string and the wall of the borehole. During the ascent, some of the mud congeals, forming a cake on the exposed face of the wellbore, for example, to prevent the mud from being lost to the porous drilled formation. In addition, the pressure inside the formation can be partially or fully counterbalanced by the hydrostatic weight of the mud column in the hole. Since the mud has a variety of vital drilling functions, it must accordingly have comparable and reliable capabilities.

Many drilling parameters, such as measured depth, string rotary speed, weight on bit, downhole torque, surface torque, flow in, surface pressure, down hole pressure, bit orientation, bit deflection, etc., can be made available in real time. However, many drilling fluid properties—which can be critical to effective hydraulic modeling and hole cleaning performance—are not readily available in real time. Historically, a technician (or "mud engineer") was required to perform a mud check once or twice every 12 hours, and report the measurement data every 24 hours. These measurements may include: density, rheology, electrical stability, filtration control, retort analysis (% solids, oil-water ratio), acidity (ph), salinity, and particle size distribution. This practice is accepted throughout the drilling industry; nevertheless, there are significant benefits to having the key mud properties tested and reported at multiple intervals designated by the operator. The on-site mud engineer, for example, typically has numerous other responsibilities in his/her daily routine and therefore cannot provide a constant stream of drilling fluid properties to a monitoring center, such as a remote real-time center. In addition, taking and/or generating such measurements are time consuming and inherently susceptible to human error. Automated mud measuring eliminates these drawbacks.

There are many systems available for measuring some of the characteristics of drilling mud. Sampling drilling fluid for instrumentation measurements, however, has many problems. Most drilling fluids are designed to plug small holes in the formation and are therefore heavily laden with solids. Moreover, the characteristics of the drilling fluid are constantly changing due to additions of solids and chemicals that make drawing a representative sample difficult. Partially suspended solids and partially dispersed chemicals can form pliable lumps that can plug sampling equipment. If left static, the solids in the drilling fluid tend to settle and plug small diameter tubing, valves, pumps and other fluid handling equipment.

There are various types of liquid-based drilling fluids: (1) water-based muds (WBM), which typically comprise a water-and-clay based composition, (2) oil-based muds (OBM), where the base fluid is a petroleum product, such as diesel fuel, and (3) synthetic-based muds (SBM), where the base fluid is a synthetic oil. In many cases, oil-based drilling fluids also have water or brine dispersed in the oil in significant proportions. In the course of drilling a well, a water-based fluid is often used in one section of the borehole, while an oil-based fluid will be used in a different section of the borehole. Switching between fluid types is fraught with problems for the sampling system and instrumentation because a thick sludge can form where the two fluid types come in contact with each other, which can plug flow passages. In addition, the drilling fluid sampling equipment and measurement instrumentation is frequently located in areas of a drilling rig with a high potential of being surrounded by high concentrations of flammable gases and fluids. As such, anything capable of generating a spark in normal operation or under fault conditions must be packaged to prevent ignition of the surrounding environment.

SUMMARY

Aspects of this disclosure are directed to Automated Mud Measuring Equipment (AMME) for measuring desired drilling fluid properties. In some embodiments, the AMME includes a sample supply system, a conditioning system, and one or more measurement modules. The measurement modules each make one or more measurements of the different drilling fluid properties. The measurement modules are connected to the sample supply system, with a master module controlling the flow. The AMME can take real-time measurements, which can provide up-to-date density and rheology data to predict accurate drilling hydraulics and its impact on drilling operations.

While drilling, much effort is expended to maximize Rate of Penetration (ROP) to minimize drilling cost. Oftentimes, computational models are used to determine the ROP limits.

Thus, current and accurate density and rheology of the fluid being pumped down hole is typically required to maximize the ROP and to have confidence in the resultant recommendations. In the above example, data from the AMME can be sent to a database, such as the Sperry Drilling Services INSITE® database and data management service, available from Halliburton. From there, the data can be processed in a Real-time Operations Center (ROC) by a hydraulics modeling software simulator, like the DFG™ Software with DrillAhead® Hydraulics Module, also available from Halliburton. The results can then be analyzed to make ROP and other operational recommendations to the rig, such as drill-pipe rotational speed (RPM), drilling fluid pump rate, fluid formulation/additions (e.g., changes to the drilling fluid composition such as adding weight material to increase the mud density or adding emulsifier, oil and brine to adjust the oil/water ratio), etc.

Other opportunities are possible for this real-time concept of fluid management. Computational models, like those generated by the DFG™ DrillAhead® Hydraulics Module, can predict ahead of the drill bit, for example, anticipating the Equivalent Circulation Density (ECD)—e.g., the increase in bottomhole pressure expressed as an increase in pressure that occurs when the mud is being circulated. Such predictions may include cuttings loading in the mud and its effect on the ECD, mud temperature throughout the wellbore, the circulating pressure drop, swab and surge pressures as the drill string is removed from or returned to the wellbore, estimated time required to completely remove drilled cuttings from the wellbore, how accumulated cuttings beds will affect ECD, etc. This allows operators to make changes to drilling procedures and the drilling fluid properties in anticipation of the coming requirements.

A similar approach can be utilized for problem zone management. A "problem zone" is a portion of the wellbore trajectory that may be difficult to drill, for example, because of the type of formation, the pore pressure of fluids in the formation (abruptly higher or lower), a formation that has fractures of rock cavities (or "vugs") which may cause some of the mud to flow into the formation ("lost circulation"), a formation that changes when exposed to the drilling fluid (e.g., swelling clays), and/or a weak formation that will be easily cracked by high ECD. A problem zone may exist and be expected at some depth while drilling. Since the current properties of the drilling fluid are known in real-time, and the properties that will be needed to drill the upcoming problem strata can be established, computational Artificial Neural Network (ANN) algorithms, for example, can be used to anticipate the fluid requirements in terms of product additions and conditioning such that when the trouble zone depth is reached the fluid is already in place and being pumped seamlessly.

In another embodiment, multiple AMME measurements can be used to characterize other well-site process efficiencies. For instance, electrical stability (ES) may be used to determine "additions control" of the drilling fluid system. That is, if ES is measured at the flow line as it comes from the well bore it can be analyzed, possibly using ANNs, to determine how the ES has changed since it was pumped down the wellbore. The ANN could then determine what, if any, product treatments or other "additions" must be added before and/or after the solids control part of the process. The treatments of additions may be manually or automatically accomplished. In addition to determining additions control, the ES may be used to determine "solids control" efficiency. Solids control efficiency can be a comparison of the ES measured after the cuttings-entrained mud comes out of the well, and again after the cuttings are removed from the mud, which may give an indication of the efficiency of the removal process. In this case, the ES is measured in multiple locations and the differences from one location to the other can define the proper treatments and efficiencies of the processes. In addition to ES, other real-time (RT) measurements could be used in the process. As each component is included in the analysis, a greater understanding of the drilling fluid properties is achieved, providing essential data for drilling optimization.

According to aspects of the present disclosure, a fluid analysis system for determining at least one characteristic of a drilling fluid is presented. The fluid analysis system includes a pump, first and second reversible fluid ports, a valve, and at least one measurement module. Each reversible fluid port is configured, when in a first state, to intake drilling fluid into the fluid analysis system and, when in a second state, to expel drilling fluid from the fluid analysis system. The valve fluidly couples the first and second reversible fluid ports to the pump. The valve is configured to control the respective states of the reversible fluid ports. The at least one measurement module is fluidly coupled to the pump to receive drilling fluid therefrom. The at least one measurement module is configured to determine at least one characteristic of the received drilling fluid.

Other aspects of the present disclosure are directed to a fluid analysis system for determining one or more characteristics of a drilling fluid. The fluid analysis system includes a pump configured to move drilling fluid through the analysis system. The fluid analysis system also includes first and second reversible fluid ports, each of which is configured to switch between an intake and an outlet state. The reversible fluid ports are configured to intake a sample of the drilling fluid when in the intake state, and to expel the sample of drilling fluid when in the outlet state. A first filter is fluidly coupled with the first reversible fluid port, while a second filter is fluidly coupled with the second reversible fluid port. A flow reversal valve fluidly couples the first and second reversible fluid ports to the pump. The flow reversal valve is configured to selectively change the respective states of the first and second reversible fluid ports between the intake and outlet states. A controller is operatively connected to and configured to control the flow reversal valve and the pump. A plurality of measurement modules is fluidly coupled (e.g., in parallel) to the pump and the flow reversal valve. Each measurement module is configured to measure a respective characteristic of the drilling fluid and output a signal indicative thereof.

In accordance with other aspects, a method of operating a drilling fluid monitoring and analysis system is also featured. The method includes, inter alia: drawing a sample of drilling fluid into the analysis system via a first reversible fluid port of the drilling fluid analysis system; determining, via a measurement module of the drilling fluid analysis system, at least one characteristic of the drilling fluid sample; generating, via the measurement module, a signal indicative of the at least one characteristic; reversing the first reversible fluid port from an intake state to an outlet state such that drilling fluid is expelled therefrom; and reversing a second reversible fluid port from an outlet state to an intake state such that the second reversible fluid port draws drilling fluid into the analysis system.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of the exemplary embodiments and modes for carrying out the present invention when taken in connection with the accompanying drawings and appended claims.

Figure 1:
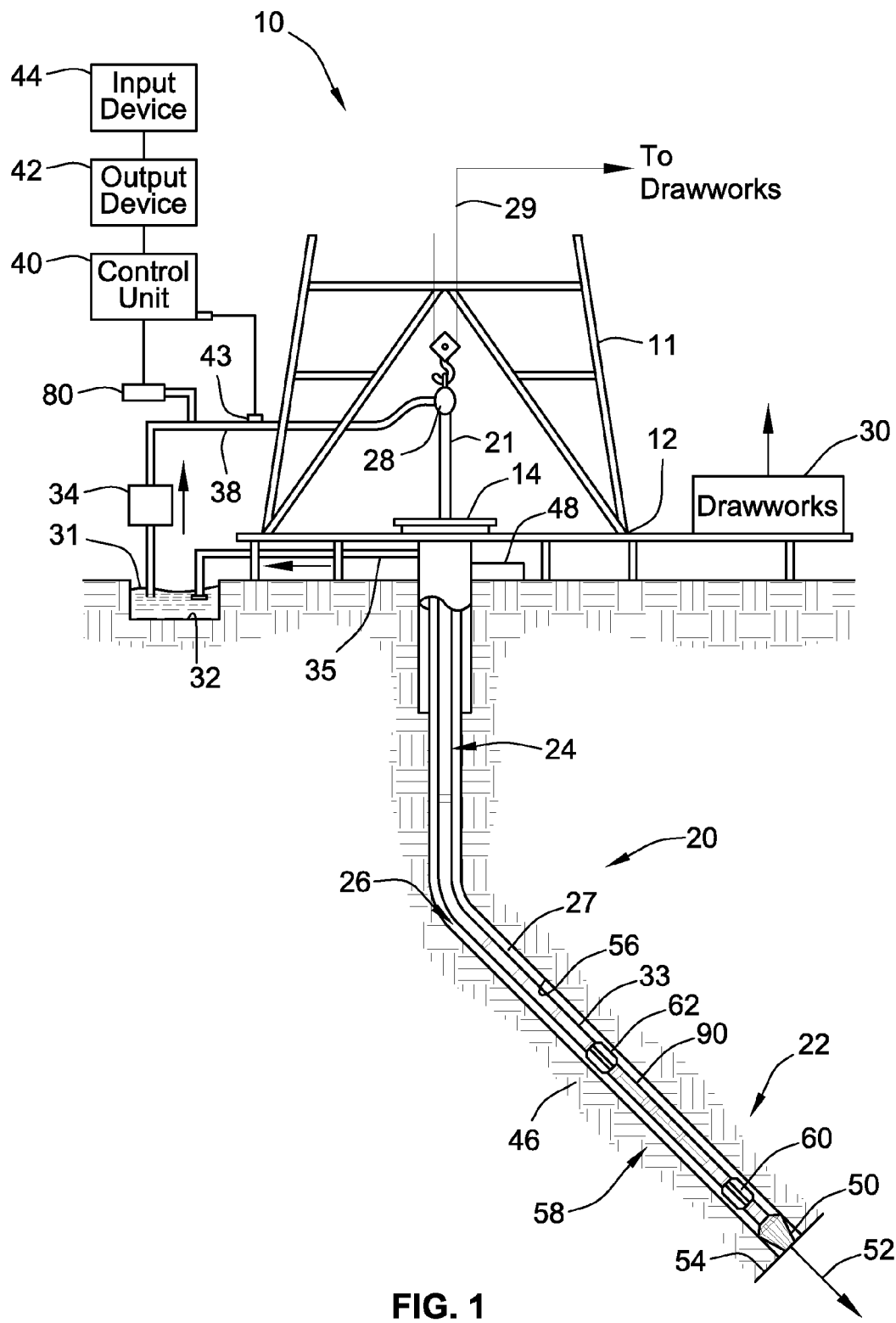
FIG. 1 is a schematic illustration of an exemplary drilling system in accordance with aspects of the present disclosure.

While the present disclosure is susceptible to various modifications and alternative forms, specific embodiments have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

While this invention is susceptible of embodiment in many different forms, there are shown in the drawings and will herein be described in detail embodiments of the invention with the understanding that the present disclosure is to be considered as an exemplification of the principles of the invention and is not intended to limit the broad aspects of the invention to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference or otherwise. For purposes of the present detailed description, unless specifically disclaimed, the singular includes the plural and vice versa unless specifically disclaimed; the words "and" and "or" shall be both conjunctive and disjunctive unless specifically disclaimed; the word "all" means "any and all"; the word "any" means "any and all"; and the word "including" means "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

Referring now to the drawings, wherein like reference numerals refer to like components throughout the several views, FIG. 1 illustrates an exemplary directional drilling system, designated generally as 10, in accordance with aspects of the present disclosure. Many of the disclosed concepts are discussed with reference to drilling operations for the exploration and/or recovery of subsurface hydrocarbon deposits, such as petroleum and natural gas. However, the disclosed concepts are not so limited, and can be applied to other drilling operations. To that end, the aspects of the present disclosure are not necessarily limited to the arrangement and components presented in FIGS. 1 and 2. For example, many of the features and aspects presented herein can be applied in horizontal drilling applications and vertical drilling applications without departing from the intended scope and spirit of the present disclosure. In addition, it should be understood that the drawings are not necessarily to scale and are provided purely for descriptive purposes; thus, the individual and relative dimensions and orientations presented in the drawings are not to be considered limiting. Additional information relating to directional drilling systems can be found, for example, in U.S. Patent Application Publication No. 2010/0259415 A1, to Michael Strachan et al., which is entitled "Method and System for Predicting Performance of a Drilling System Having Multiple Cutting Structures" and is incorporated herein by reference in its entirety.

The directional drilling system 10 exemplified in FIG. 1 includes a tower or "derrick" 11, as it is most commonly referred to in the art, that is buttressed by a derrick floor 12. The derrick floor 12 supports a rotary table 14 that is driven at a desired rotational speed, for example, via a chain drive system through operation of a prime mover (not shown). The rotary table 14, in turn, provides the necessary rotational force to a drill string 20. The drill string 20, which includes a drill pipe section 24, extends downwardly from the rotary table 14 into a directional borehole 26. As illustrated in the Figures, the borehole 26 may travel along a multi-dimensional path or "trajectory." The three-dimensional direction of the bottom 54 of the borehole 26 of FIG. 1 is represented by a pointing vector 52.

A drill bit 50 is attached to the distal, downhole end of the drill string 20. When rotated, e.g., via the rotary table 14, the drill bit 50 operates to break up and generally disintegrate the geological formation 46. The drill string 20 is coupled to a "drawworks" hoisting apparatus 30, for example, via a kelly joint 21, swivel 28, and line 29 through a pulley system (not shown). The drawworks 30 may comprise various components, including a drum, one or more motors, a reduction gear, a main brake, and an auxiliary brake. During a drilling operation, the drawworks 30 can be operated, in some embodiments, to control the weight on bit 50 and the rate of penetration of the drill string 20 into the borehole 26. The operation of a drawworks 30 is generally known and is thus not described in detail herein.

During drilling operations, a suitable drilling fluid (commonly referred to in the art as "mud") 31 can be circulated, under pressure, out from a mud pit 32 and into the borehole 26 through the drill string 20 by a hydraulic "mud pump" 34. The drilling fluid 31 may comprise, for example, water-based muds (WBM), oil-based muds (OBM), synthetic-based muds (SBM), as well as gaseous drilling fluids, singly and in any logical combination. Drilling fluid 31 passes from the mud pump 34 into the drill string 20 via a fluid conduit (commonly referred to as a "mud line") 38 and the kelly joint 21. Drilling fluid 31 is discharged at the borehole bottom 54 through a nozzle or other opening in the drill bit 50, and circulates in an "uphole" direction towards the surface through an annular space 27 between the drill string 20 and the side of the borehole 56. As the drilling fluid 31 approaches the rotary table 14, it is discharged via a return line 35 into the mud pit 32. A variety of surface sensors 48, which are appropriately deployed on the surface of the borehole 26, operate alone or in conjunction with downhole sensors 70, 72 deployed within the borehole 26, to provide information about various drilling-related parameters, such as fluid flow rate, weight on bit, hook load, etc., some of which will be explained in further detail below.

A surface control unit 40 may receive signals from surface and downhole sensors and devices via a sensor or transducer 43, which can be placed on the fluid line 38. The surface control unit 40 can be operable to process such signals according to programmed instructions provided to surface control unit 40. Surface control unit 40 may present to an operator desired drilling parameters and other information via one or more output devices 42, such as a display, a computer monitor, speakers, lights, etc., which may be used by the operator to control the drilling operations. Surface control unit 40 may contain a computer, memory for storing data, a data recorder, and other known and hereinafter developed peripherals. Surface control unit 40 may also include models and may process data according to programmed instructions, and respond to user commands entered through a suitable input device 44, which may be in the nature of a keyboard, touchscreen, microphone, mouse, joystick, etc.

In some embodiments of the present disclosure, the rotatable drill bit 50 is attached at a distal end of a steerable drilling bottom hole assembly (BHA) 22. In the illustrated embodiment, the BHA 22 is coupled between the drill bit 50 and the drill pipe section 24 of the drill string 20. The BHA 22 may comprise a Measurement While Drilling (MWD) System, designated generally at 58 in FIG. 1, with various sensors to provide information about the formation 46 and downhole drilling parameters. The MWD sensors in the BHA 22 may include, but are not limited to, a device for measuring the formation resistivity near the drill bit, a gamma ray device for measuring the formation gamma ray intensity, devices for determining the inclination and azimuth of the drill string, and pressure sensors for measuring drilling fluid pressure downhole. The MWD may also include additional/alternative sensing devices for measuring shock, vibration, torque, telemetry, etc. The above-noted devices may transmit data to a downhole transmitter 33, which in turn transmits the data uphole to the surface control unit 40. In some embodiments, the BHA 22 may also include a Logging While Drilling (LWD) System.

In some embodiments, a mud pulse telemetry technique may be used to communicate data from downhole sensors and devices during drilling operations. Exemplary methods and apparatuses for mud pulse telemetry are described in U.S. Pat. No. 7,106,210 B2, to Christopher A. Golla et al., which is incorporated herein by reference in its entirety. Other known methods of telemetry which may be used without departing from the intended scope of this disclosure include electromagnetic telemetry, acoustic telemetry, and wired drill pipe telemetry, among others.

A transducer 43 can be placed in the mud supply line 38 to detect the mud pulses responsive to the data transmitted by the downhole transmitter 33. The transducer 43 in turn generates electrical signals, for example, in response to the mud pressure variations and transmits such signals to the surface control unit 40. Alternatively, other telemetry techniques such as electromagnetic and/or acoustic techniques or any other suitable techniques known or hereinafter developed may be utilized. By way of example, hard wired drill pipe may be used to communicate between the surface and downhole devices. In another example, combinations of the techniques described may be used. As illustrated in FIG. 1, a surface transmitter receiver 80 communicates with downhole tools using, for example, any of the transmission techniques described, such as a mud pulse telemetry technique. This can enable two-way communication between the surface control unit 40 and the downhole tools described below.

According to aspects of this disclosure, the BHA 22 provides the requisite force for the bit 50 to break through the formation 46 (known as "weight on bit"), and provide the necessary directional control for drilling the borehole 26. In the embodiments illustrated in FIGS. 1 and 2, the BHA 22 may comprise a drilling motor 90 and first and second longitudinally spaced stabilizers 60 and 62. At least one of the stabilizers 60, 62 may be an adjustable stabilizer that is operable to assist in controlling the direction of the borehole 26. Optional radially adjustable stabilizers may be used in the BHA 22 of the steerable directional drilling system 10 to adjust the angle of the BHA 22 with respect to the axis of the borehole 26. A radially adjustable stabilizer provides a wider range of directional adjustability than is available with a conventional fixed diameter stabilizer. This adjustability may save substantial rig time by allowing the BHA 22 to be adjusted downhole instead of tripping out for changes. However, even a radially adjustable stabilizer provides only a limited range of directional adjustments. Additional information regarding adjustable stabilizers and their use in directional drilling systems can be found in U.S. Patent Application Publication No. 2011/0031023 A1, to Clive D. Menezes et al., which is entitled "Borehole Drilling Apparatus, Systems, and Methods" and is incorporated herein by reference in its entirety.

Figure 2:
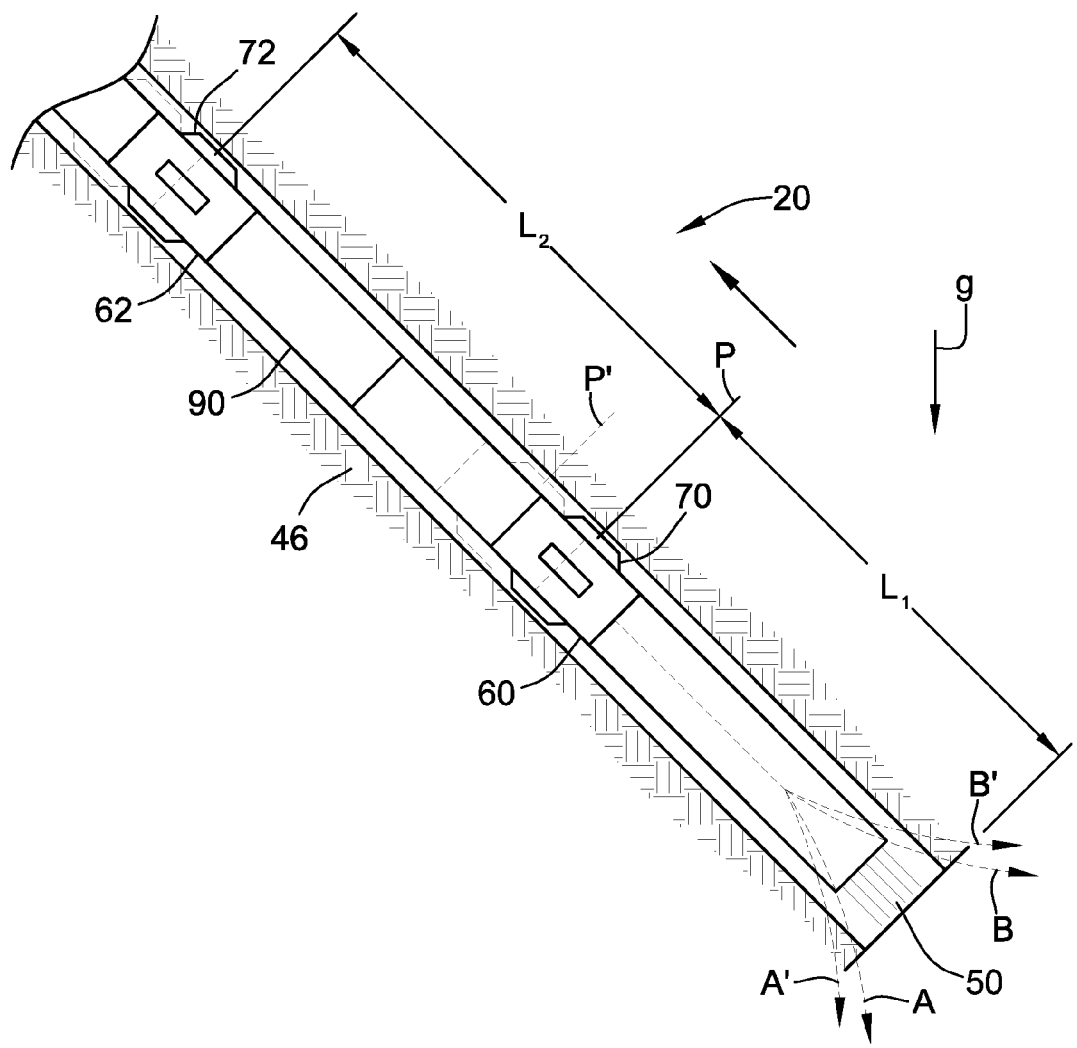
FIG. 2 is a schematic illustration of an exemplary bottom hole assembly (BHA) in accordance with aspects of the present disclosure.

As shown in the embodiment of FIG. 2, the distance between the drill bit 50 and the first stabilizer 60, designated as $L_1$, can be a factor in determining the bend characteristics of the BHA 22. Similarly, the distance between the first stabilizer 60 and the second stabilizer 62, designated as $L_2$, can be another factor in determining the bend characteristics of the BHA 22. The deflection at the drill bit 50 of the BHA 22 is a nonlinear function of the distance $L_1$, such that relatively small changes in $L_1$ may significantly alter the bending characteristics of the BHA 22. With radially movable stabilizer blades, a dropping or building angle, for example A or B, can be induced at bit 50 with the stabilizer at position P. By axially moving stabilizer 60 from P to P', the deflection at bit 50 can be increased from A to A' or B to B'. A stabilizer having both axial and radial adjustment may substantially extend the range of directional adjustment, thereby saving the time necessary to change out the BHA 22 to a different configuration. In some embodiments the stabilizer may be axially movable. The position and adjustment of the second stabilizer 62 adds additional flexibility in adjusting the BHA 22 to achieve the desired bend of the BHA 22 to achieve the desired borehole curvature and direction. As such, the second stabilizer 62 may have the same functionality as the first stabilizer 60. While shown in two dimensions, proper adjustment of stabilizer blades may also provide three dimensional turning of BHA 22.

Figure 3:
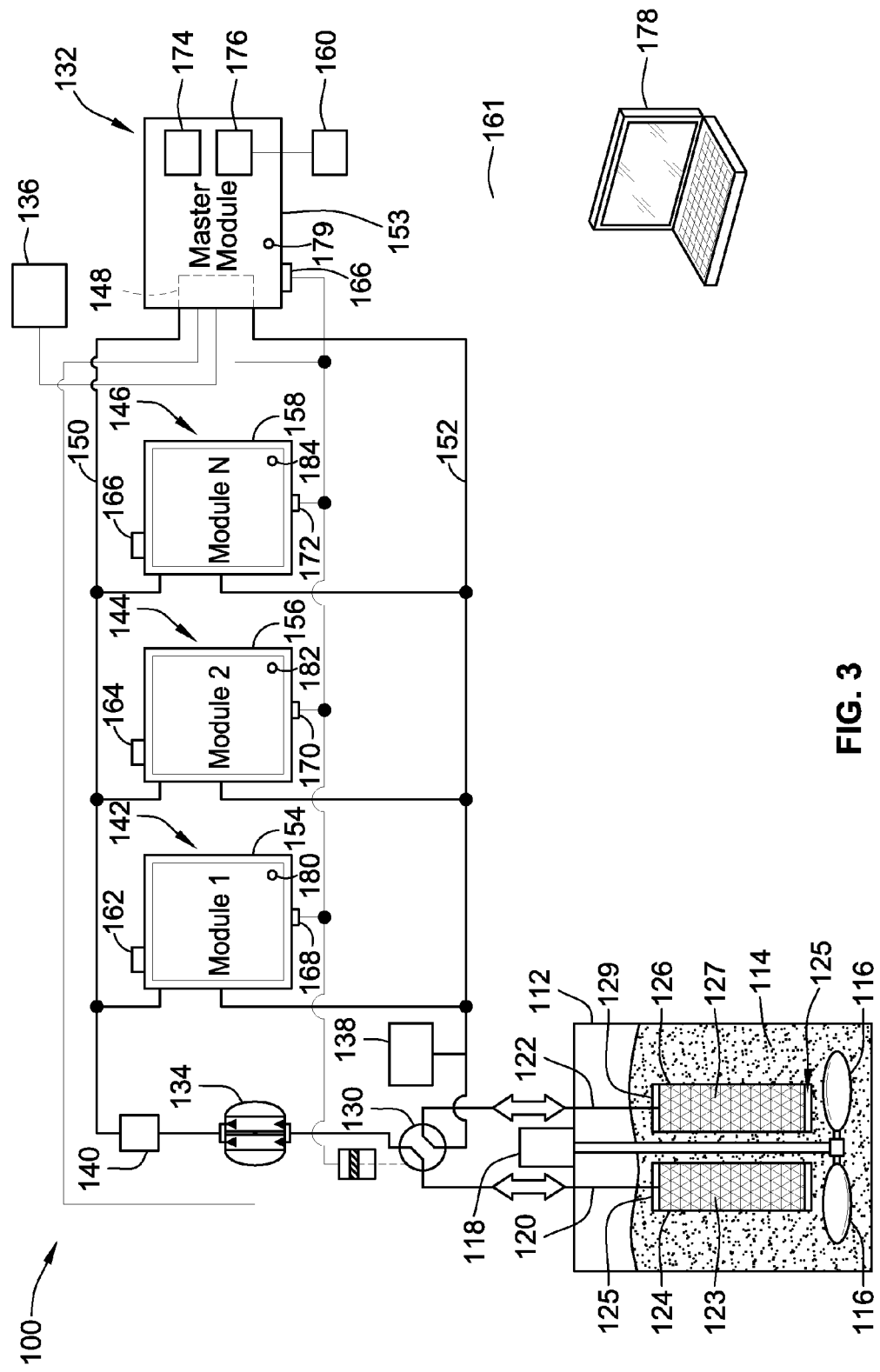
FIG. 3 is a schematic diagram of a representative drilling fluid monitoring system in accordance with aspects of the present disclosure.

Turning now to FIG. 3, a representative drilling fluid monitoring and analysis system, designated generally as 100, is shown in accordance with aspects of the present disclosure. As developed in further detail below, the monitoring system 100 is operable to monitor, measure, analyze or otherwise determine one or more characteristics of a drilling fluid, including completion fluids, pills spotting fluids, etc. For effective hydraulic modeling and hole cleaning performance, some of the most important mud properties include, singly or collectively, and without limitation, viscosity and density at a known temperature, base fluid type (e.g., water, brine oil), oil-to-water ratio, salinity of the water phase, the average specific gravity of the solids (ASG), and volume percent solids. Other mud properties could include the temperature of the mud going down hole and returning at the flow line. It may be ideal, in some embodiments, for the viscosity of the mud to be measured at a series of elevated temperatures and pressures that represents the conditions in the well at several different depths. It may also be desirable to monitor the surface ambient conditions. Additional characteristics that can be measured and/or monitored include, for example, chloride content, carbonate concentration, acidity (ph), pressurized density ("pressurized mud balance"), alkalinity, filtrate volume, sand content, sulfide concentration, retort analysis, etc.

A fluid sample can be drawn from any desired point in the drilling system. In the illustrated embodiment, for example, the sample is taken from the active mud pit 112 (or "mud tank") where the drilling fluid 114 is drawn, for example, via mud pump 34 (FIG. 1), into a well, such as the borehole 26 illustrated in FIG. 1. It should be readily understood that the fluid samples can be taken at one or more additional/alternative locations of the drilling system without departing from the intended scope of the present disclosure. To keep solids entrained in the drilling fluid from settling, the mud pit 112 may be agitated or stirred, for example, by an agitator system, which is represented herein by one or more blades 116 that are driven by a geared motor 118 mounted on top of the mud tank 112. A number of non-limiting examples of mud agitators are available from Dynamix Agitators Inc., of Richmond, British Columbia, Canada.

Sample suction and discharge ports 120 and 122, respectively, include openings located below the surface of the mud pool, but far enough from the bottom of the mud pit 112 to avoid solids that intrinsically accumulate on the bottom of the pit 112. The suction and discharge ports 120, 122 (also respectively referred to herein as "inlet and outlet ports" or "first and second reversible fluid ports") may be temporally or permanently attached to the mud pit 112 to avoid inadvertent engagement with the agitator. In some optional configurations, the monitoring system 100 includes multiple suction and/or discharge ports 120, 122, which may be distributed in a manner similar to what is shown in FIG. 3 or, alternatively, may be fluidly coupled to other sections of the mud tank 112 or other portions of the drilling system.

According to some embodiments, each of the ports 120, 122 includes a respective filter 124 and 126 configured to prevent large solids (for example, solids with a major dimension of approximately 0.5 mm or greater or, in some embodiments, 0.8 mm or greater) from entering the monitoring system 100. By way of non-limiting example, the first and second filters 124, 126 can include wire-wound screens 123 and 127, respectively, such as the triangular-shaped wire screens shown in FIG. 3. In this vein, each filtration layer can be made up of precisely spaced wires (e.g., spaced approximately 0.8 mm) that are wrapped over and welded to one or more support (or "rib") wires, e.g., to form a uniform gap. The exterior wires may be arranged so that the outer surface of the wire forms a smooth cylindrical screen over the rib wires. It is desirable, in at least some embodiments, for the wrapping wires to be strong enough to withstand internal and/or external operational pressures, typically in the nature of at least approximately 14 psi (and in some embodiments approximately 12-16 psi) on the suction side and at least approximately 100 psi (and in some embodiments approximately 85-115psi) internally on the discharge side. Appropriate caps 125 and 129 on the upper and/or lower ends of the cylindrical screen 123, 127, respectively, are configured to prevent solids from bypassing the screens 123, 127 and, in some embodiments, provide attachment points for fluid conduits (e.g., flow tubing). Flow is into, or out of, the interior of each cylindrical screen 123, 127, through the gaps in the screen wires. Alternative configurations may include other filter designs (e.g., other types of surface and depth filters) or wire screens with different shapes and patterns.

During normal operation, solids will eventually build up on the face of the filter being used for suction (e.g., first filter 124), partially plugging off the current fluid-inlet port, which is the suction port 120 in the embodiment of FIG. 3. To minimize or otherwise prevent this type of occurrence, the monitoring system 100 is operable to switch to one or more "new" inlet ports. In the illustrated embodiment, for example, a valve 130, which is controlled by a master module 132, fluidly couples the suction and discharge ports 120, 122 to a fluid pump 134. The pump 134 is configured to draw the drilling fluid 114 into and move it through the fluid analysis system 100. In the illustrated embodiment, an air operated diaphragm pump is employed; however, other pump mechanisms could also be used. Depending, for example, on the intended application, diaphragm pumps have an advantage because the flow pressure is limited to the pressure of the air supply 136 (e.g., 100 psi) and diaphragm pumps can handle fluids entrained with relatively large solids. To limit suction pressure drop, the pump 134 can be located as close as practical to the suction and discharge ports 120, 122.

The valve 130 is selectively operable to switch the flow direction of the drilling fluid into and out of the monitoring system 100. In the illustrated embodiment, for example, each of the fluid ports 120, 122 is reversible—i.e., configured to switch from a first "intake" state to a second "outlet" state, and back. When in the intake state, each port 120, 122 is configured to intake a sample/stream of the drilling fluid 114. Conversely, when in the outlet state, each port 120, 122 is configured to expel the sample/stream of the drilling fluid 114 from the monitoring system 100. It is desirable, in at least those embodiments with only two ports, that only one of the ports 120, 122 be in the intake state/outlet state at any given time. The valve 130 is configured to control the respective states of the reversible fluid ports 120, 122. As illustrated, the valve 130 includes a flow reversal valve assembly, which may take on various forms including plug valves, ball valves, pinch valves, etc. Simply put, the valve 130 changes which one of the ports 120, 122 is coupled downstream from the pump 134 to draw fluid 114 into the system 100, and which one of the ports 120, 122 is coupled upstream from the pump 134 to expel fluid 114 into the system 100. In so doing, the suction port 120 can be changed to a discharge port, and back, while the discharge port 122 is changed to a suction port, and back. The flow of drilling fluid 114 out of a port 120, 122 through a respective filter 124, 126, alone or in combination with agitation in the mud pit 112 (e.g., via blades 116), the smooth surface of the exterior of the cylindrical screen 123, 127, and/or bursts of pressurized air in the return flow from measurement instrument cleaning or a pneumatic device, such as dedicated jets 138, operates to clear buildup off of the face of the filter screen. Regularly switching the flow direction of drilling fluid 114 through the monitoring system 100 prevents most solids from building up to the point of stopping flow. Switching can be periodic and/or in response to flow pressure drop.

In some implementations, the monitoring system 100 includes one or more conditioning devices, each of which is configured to modify (and, in some embodiments, measure)

at least one property of the drilling fluid 114. By way of non-limiting example, a temperature-conditioning heat exchanger 140 is incorporated in the system 100 of FIG. 3. The heat exchanger 140 is configured to modify the inlet temperature of the drilling fluid 114 sample/stream taken into the fluid analysis system 100. As shown, the heat exchanger 140 is located upstream from the pump 134 in the flow of drilling fluid 114 after the discharge of the pump 134. Optionally or alternatively, the conditioning device 140 may include other conditioning features, such as a pressurizing device (e.g., a booster pump to minimize any entrained bubbles or gas effects) configured to increase the inlet pressure of the drilling fluid 114 taken into the fluid analysis system 100. Other optional configurations may include a conditioning device configured to dilute and/or mix the fluid sample. Certain implementations require the sample drilling fluid 114 be conditioned prior to analysis because testing specifications may require the sample be at a particular temperature and/or pressure when taking measurements, e.g., viscosity or density, are taken. In many drilling scenarios, the drilling fluid 114 in the mud pit 112 may be too hot or too cold to meet testing specs; without the conditioning device(s), a considerable amount of time would be wasted waiting for the fluid samples to naturally realize requisite measurement temperatures within the measurement module.

After leaving the optional conditioning device(s), the drilling fluid 114 sample flows to one or more measurement modules, which are represented in FIG. 3 by first, second and nth modules 142, 144 and 146, respectively. Although three measurement modules 142, 144, 146 are shown (four when including the master module 132), any number of modules may be incorporated into the monitoring system 100. The master module 132 and measurement modules 142, 144, 146 are fluidly coupled to the pump 134 and, in some optional configurations, the conditioning device 140 to receive drilling fluid 114 therefrom. The master and measurement modules 132, 142, 144, 146 of FIG. 3 are shown connected in parallel; however, it is envisioned that one or more of the modules be connected in series. Each of the measurement modules 142, 144, 146 (and, in some embodiments, the master module 132) is configured to measure, monitor, analyze or otherwise determine at least one characteristic of the received drilling fluid 114. The modules 132, 142, 144, 146 of FIG. 3 are each fluidly coupled to both the supply line 150 and the return line 152. In some implementations, a continuous or substantially-continuous stream of drilling fluid 114 is pumped past the modules 142, 144, 146, through a bypass 148 in the master module 132, and back to the sample source (e.g., mud pit 112) via the valve 130. In some applications, all or a part of the sample flow can pass through a particular module 142, 144, 146, or a combination thereof. The modules 132, 142, 144, 146 may take make measurements that require the mud 114 be heated, pressurized, diluted, or otherwise conditioned before taking measurements. This can be handled as a batch process where a sample is drawn, conditioned, measured and expelled. This cycle can be repeated as required. In some configurations the sample used in testing may not be returned to the fluid system, but may be directed to a waste container. For example, if a test required extensive dilution or special chemicals it may be advisable to discard the sample.

In testing scenarios where a measurement can be made, for example, at ambient sample conditions, the fluid sample may flow through one or more of the modules 142, 144, 146 in series. By way of clarification, and not limitation, series connections of the measurement modules 142, 144, 146 are generally most suitable when the drilling fluid 114 is not changed by the measurement, e.g., there is no significant pressure drop, dilution or contamination caused by passage of the mud 114 through the measurement module 142, 144, 146. An example of such a measurement is the ambient density measurement in the Real Time Density and Viscosity (RTDV) module, which will be developed further below.

The monitoring system 100 may be located in areas with a high potential of being exposed to flammable gases and fluids. Each of the modules 132, 142, 144, 146 may therefore incorporate a protection system and/or a suitable enclosure 153, 154, 156 and 158, respectively, to permit operation in flammable atmospheres and for protection from exposure to flammable elements. Flammable atmosphere protection can be provided by an air- and/or nitrogen-purged enclosure, or an explosion-proof enclosure designed to industry-accepted standards for such hazards. Some such standards are available from organizations like the National Fire Protection Association (NFPA) and Det Norske Veritas (DNV). For a purged enclosure, a sheet metal box can be employed which includes an access door with seals. Standardized boxes of this type are available from the National Electrical Manufacturers Association (NEMA). By way of non-limiting example, the enclosure can be in the nature of a Wiegmann SSN4362012, Enclosure 304 Stainless Steel, NEMA Type 4x, with a height of approximately 36 in, a width of approximately 30 in, and a depth of approximately 12 in.

In some embodiments, each module 132, 142, 144, 146 is supplied with at least approximately 100 psi clean air (and in some embodiments approximately 90-110 psi), for example, from a common air supply 136. Each enclosure 153, 154, 156 and 158 may also include connections that provide pressurized water or base-oil as needed. A power source 160 can provide each module 132, 142, 144, 146 with electrical power to suit its particular requirements. Each module 132, 142, 144, 146 can also be equipped with a means 161, 162, 164 and 166, respectively, of digital communications. Typically, this would include a wired or wireless Ethernet connection. Alternative means of communication are also envisioned. Several serial and parallel communications protocols can be used. An example would be the serial RS-485 standard. When the communications take place in a hazardous environment, such as those described above, it may be desirable for the communication devices 161, 162, 164, 166 to also meet hazardous environment safety regulations.

One of the key factors in module reliability is keeping the sample flow path clean. Each of the modules 132, 142, 144, 146 may therefore be provided with air injection ports 165, 168, 170 and 172, respectively, for introducing pressurized air into and thereby cleaning the drilling fluid flow passages of the module. Air injection provides a highly turbulent agitation that helps re-suspend settled solids and move them toward the sample return line 152. Air is also compatible with most types of drilling fluids and does not form a sludge that will plug the apparatus. Automatic and/or manual air injection can also be used to flush drilling fluid and settled fluids from the modules 132, 142, 144, 146 during normal automatic operation, prior to long term shutdowns, and/or between drilling fluid types. When needed, the infusion of air can be followed by circulating a suitable cleaning fluid through the entire system 100 by means of the system pump 134. This process can be manual or automated. Each air injector 168, 170, 172 can be protected by a redundant back-flow check valve and/or other means to prevent flow of the drilling fluid 114 into the air supply 136 if the air supply pressure drops below the sample pressure.

The master module 132 includes one or more controllers 174, such as the National Instruments cRIO-9012, to control the valve 130, the pump 134, and the measurement modules

142, 144, 146. The controller(s) may be operable to provide additional functions. By way of example, complex algorithms, such as Herschel-Bulkley formulas for rheology modeling, can be stored in a memory device 176 and implemented by the controller(s); the results can then be transmitted—e.g., via cabling or wireless signal, to the user via a user interface or host data server 178, such as personal computing device or other system with, for example, a display screen, server, audio speakers, etc. The measurement data from the modules 132, 142, 144, 146 can be comprised of multiple variables from a single instrument as well as multiple variables from multiple instruments, a single variable per instrument, etc. Measurements, such as time, temperature, shear stress, breakdown voltage, etc., are packaged with a common markup language, such as XML, which allows the data to be easily transmitted to users on the drilling rig or at remote locations, such as a Real-time Operations Center (ROC). Also, the computer provides for the further packaging of the XML transmissions into other languages, such as the newest WITSML standard. This provides for a direct data exchange to a WITSML server, allowing the instrument to by-pass data acquisition systems.

Each of the modules 123, 142, 144, 146 can be provided with alarm and fault-reporting capabilities. The electrical power source 160 and air supply 136 may be subject to occasional interruptions. As an optional protective measure, one or more of the modules 132, 142, 144, 146 can be provided with a fault detection sensor 179, 180, 182 and 184, respectively, configured to detect the occurrence of a fault event (e.g., an inadvertent lapse in power) and, in some embodiments, operate (e.g., with the master module 132) to safely shutdown the monitoring system 100 in a way that protects the system hardware. Where appropriate, when interrupted services are restored, one or more of the modules 132, 142, 144, 146 may be operable to independently restart itself without user intervention to minimize data loss. When external communications are interrupted, data is stored (e.g., in memory device 176) for future transmission or retrieval. In some embodiment, one or more of the modules 132, 142, 144, 146 is configured to measure a characteristic of drilling fluids at elevated temperature and pressures.

With continuing reference to FIG. 3, the master module 132 may be configured to measure the rheology (e.g., viscosity, shear rate) and density (kg/m$^3$) of the drilling fluid 114 sample in addition to controlling the sample flow through the monitoring system 100. The master module 132 is also operable to control the flow of air to the diaphragm pump 134 and/or to the flow reversal valve 130. In some embodiments, the master module 132 allows a continuous flow of the fluid sample to pass therethrough and can selectively divert or otherwise distribute fluid to the other modules 142, 144, 146. To provide sufficient pressure for the upstream measurement modules, the flow (e.g., through the bypass 148) can be stopped at the master module 132 when needed. This can raise the pressure in the sample supply line 150 to near the diaphragm pump air supply pressure—e.g., about 80 psi. This provides sufficient pressure to push the sample drilling fluid 114 into the measurement module 142, 144, 146 requiring a sample.

Figure 4:
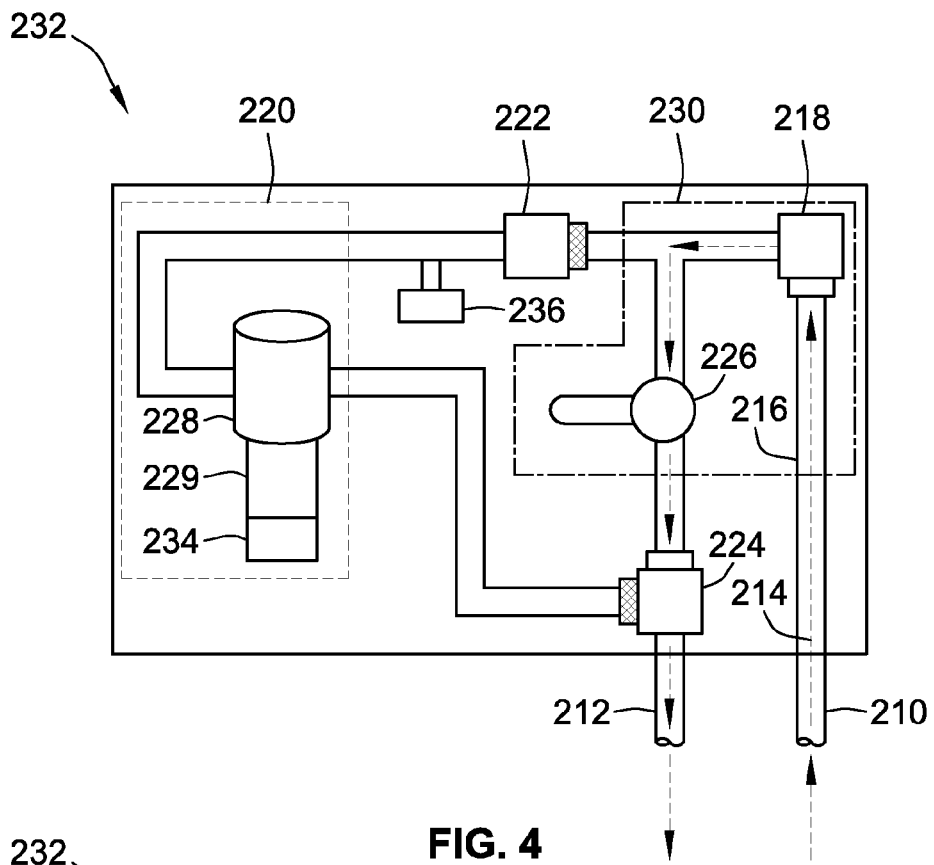
FIG. 4 is a schematic diagram of a representative master module in accordance with aspects of the present disclosure shown preparing to measure drilling fluid density.
Figure 5:
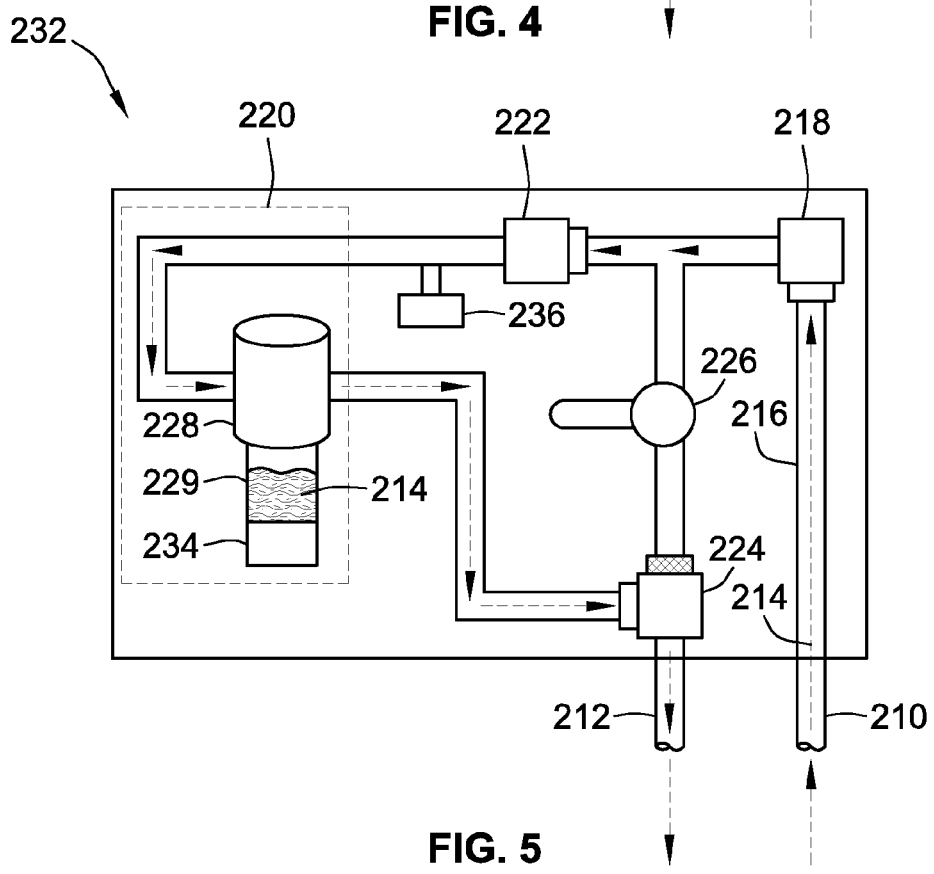
FIG. 5 illustrates the representative master module of FIG. 4 measuring drilling fluid viscosity.

According to some embodiments, the master module 132 is a Real-time Density and Viscosity (RTDV) device, designated generally as 232 in FIGS. 4 and 5, available from Halliburton, which is a fully automated measurement unit designed to measure the density and rheological properties of a drilling fluid per API standards. The unit is designed to reside at a drilling rig location (e.g., skid or wall mounted), and is continuously (or periodically) supplied with drilling fluid from the sample supply system. Measurements can be performed at an average frequency of 1 test per 20 minutes and data can be collected, for example, via the Sperry Drilling Services INSITE® database and data management service, also available from Halliburton. The system allows for customizable sorting of the data and viewing via INSITE®. As seen in FIG. 4, drilling fluid enters the RTDV 232 through a "fluid in" connection 210, and flows through internal fluid conduits (e.g., stainless steel tubing) 216 to a pneumatic, 2-way inlet valve 218. The inlet valve 218 is normally in the open position allowing the fluid sample 214 to flow to other sections of the tubing 216. Closing of the inlet valve 218 is typically performed when multiple measurement modules (e.g., measurement modules 142, 144, 146 of FIG. 3) are in use, and the multiple modules share a common fluid supply line (e.g., supply line 150). By closing inlet valve 218, the flow of drilling fluid 214 is effectively stopped from entering the RTDV 232, and the full fluid flow 214 is forced to the previous modules in the supply line.

Under normal flow conditions, the sample drilling fluid 214 flows through the inlet valve 218, and is blocked from entering the viscosity flow loop 220 portion of the RTDV 232 via a pneumatic, 2-way intermediate valve 222. Valve 222 position is normally closed. This diverts the sample drilling fluid 214 into the tubing section which contains a density transducer 226, which may be in the nature of an L-Dens 427 Density Sensor with an accuracy of at least approximately $1 \times 10^{-4}$ g/cm$^3$, available from Anton Paar. After measurements are taken by the density transducer 226, the fluid sample 214 eventually exits the RTDV 232 via a "fluid out" connection 212 to the return flow line (e.g., return line 152 of FIG. 3). In particular, the flow of the fluid 214 continues past the density transducer 226 and enters a pneumatic, 3-way outlet valve 224. Valve 224 is normally positioned such that the fluid in the viscosity flow loop 220 is blocked, and fluid flow for the density flow loop 230 is allowed to pass through the outlet valve 224 and exit the RTDV 232 through the "fluid out" connection 212.

In some embodiments, an optional throttled bypass around the density transducer 226 allows a (major) portion of the flow to bypass, minimizing transducer wear and the pressure drop through the density transducer 226. As the fluid flows through the density transducer 226, the density and the temperature of the drilling fluid sample 214 are measured and the data is recorded in the RTDV 232, e.g., via controller 174 and memory device 176. When operating in this manor, density measurements are typically performed at the temperature of the sample provided via the supply system. In an optional implementation, the density transducer 226 can be located in the viscosity flow loop 220, which can use a batch process to heat and pressurize the fluid sample 214 to predetermined conditions. Density measurements at pressures above ambient can reduce measurement errors caused by entrainment of gas bubbles in the sample. In some cases it may be desirable to incorporate density transducers in both locations.

Turning now to FIG. 5, to perform rheology measurements, the flow of the drilling fluid sample 214 is diverted from the density flow loop 230 into a "secondary" tubing loop that can be isolated and pressurized. This secondary loop is considered the viscosity flow loop 220, and includes a viscometer 228, which may be in the nature of a modified TT-100 In-Line Viscometer, available from Brookfield Engineering Laboratories, Inc. Additional information regarding the operation of and the aforementioned modifications to a Brookfield TT-100 Viscometer is presented, for example, by Robert Murphy and Dale Jamison in "Viscometer Modifications to Improve Accuracy and Performance in Real-time Field Applications", which is incorporated herein by reference in its entirety.

Diversion of the fluid sample 214 into this viscosity flow loop 220 is accomplished through the actuation of intermediate valve 222 into an open position, as seen in FIG. 5, allowing fluid flow therethrough. Concurrently, the 3-way outlet valve 224 is pneumatically actuated such that flow from the density flow loop 230 is diverted and fluid flow from the viscosity flow loop 220 is allowed to enter outlet valve 224 and exit the RTDV 232 through the "fluid out" connection 212. As the drilling fluid sample 214 flows through the viscosity flow loop 220, the viscometer 228 measurement chamber 229 is filled with a fresh sample of the drilling fluid 214. Optionally, a predefined or user-defined time period in which the fluid 214 is diverted through the viscosity flow loop 220 can be input and/or adjusted through an RTDV computer interface (not shown). In at least some embodiments, after the user-defined time for fluid flow 214 through the viscosity flow loop 220 has expired, the fluid flow 214 reverts to the density flow loop 230.

Once the fluid flow 214 has reverted to the density flow loop 230, the sample drilling fluid 214 which remains in the measurement chamber 229 is effectively isolated within the viscosity flow loop 220. The fluid sample 214 within the measurement chamber 229 is then pressurized (e.g., to greater than approximately 80 psi) to collapse any entrained air bubbles that may be present within the sample. The pressurized sample can then be agitated within the measurement chamber 229 while the temperature of the sample is adjusted to a user defined setting (e.g., approximately 120° F.-150° F.). Heating of the fluid sample 214 can be accomplished by the use of dual 100-watt cartridge heaters 234 which reside within an aluminum block. The aluminum block can saddle the measurement chamber 229, and allows heat transfer from the cartridge heaters 234 to the measurement chamber 229. Heating of the measurement chamber 229 provides heat transfer to the fluid sample 214 within. Once a predefined or user-defined fluid sample temperature is obtained, a measure of the fluid's shear stress is taken, for example, at six (6) various rpm points. Standard rpm points are determined by the American Petroleum Institute (API) as 600, 300, 200, 100, 6 and 3 revolutions per minute. Since the measurement geometry of the API type concentric-cylinder rheometer is different from that used in the Brookfield TT-100, the actual measurement rpm can be adjusted to give the equivalent shear rate.

After one or more rheology measurements have been made, the fluid flow path is again diverted from the density flow loop 230 into the viscosity flow loop 220. A burst of pressurized air from a pneumatic system 236 can be injected into the measurement chamber 229, e.g., for 1-5 seconds, to help expel the sample 214 and break loose any buildup of solids from the sample 214. Introduction of a fresh sample into the viscosity flow loop 220 will operate to flush the previous fluid sample from the measurement chamber 229. After the viscometer 228 is filled with a new drilling fluid sample 214, the above process can be repeated.

The measurement modules 142, 144, 146 can individually or collectively take on various different formats, designs and configurations to measure any one or more of a multitude of fluid characteristics. By way of non-limiting example, the first measurement module 142 may be a Real Time Emulsion Stability Tester (REST) Measurement Module which measures the electrical stability of the drilling fluid. Additional information regarding exemplary configurations and operations of REST modules may be found in U.S. Pat. No. 6,906,535 B2, to Robert J. Murphy, Jr. et al., U.S. Pat. No. 7,701,229 B2, to Robert J. Murphy, Jr. et al., and U.S. Pat. No. 7,830,161 B2, to Robert J. Murphy, each of which is incorporated herein by reference in its respective entirety. The REST module provides repeatable and accurate electrical stability measurements. The testing interval can be, for example, about 3-6 minutes depending, for example, on the number of test types being run. Results can include, in some non-limiting examples, the ES break energy current wave form analysis and the delayed measurement analysis.

In another example, the second measurement module 144 can be in the nature of a Real Time Filtrate (RTFT) Measurement Module. Additional information regarding an exemplary configuration and operation of an RTFT Measurement Module can be found in U.S. Pat. No. 7,721,612 B2, to Dale E. Jamison, which is incorporated herein by reference in its entirety. An RTFT Measurement Module can measure fluid loss, spurt fluid loss, and/or filter cake thickness properties. The measurements can be done with a ceramic filter medium and/or a paper medium option. The testing interval can vary from about 2 to 4 hours. The lengthy intervals are usually due to the heat up and cool down times.

Other measurement module options include Real Time Retort (RTRT) Measurement Modules, which measure the percent oil, water and/or solids of the drilling fluid, and particle size distribution modules, which measure the sizes and relative quantities of the various particles in the drilling fluid sample. The measurements of particle size are typically limited to particles larger than one micron and smaller than about 1000 microns. The master module 132 can be (in some embodiments, is preferably) a measurement module that is built similar to one or more of the measurement modules 142, 144, 146.

Drilling fluid property measurement procedures and equipment have long been specified by the American Petroleum Institute (API) and various other organizations. Two exemplary API regulations include API RP 13B-1, "Recommended Practice for Field Testing Water-based Drilling Fluids," and RP 13B-2, "Recommended Practice for Field Testing Oil-based Drilling Fluids," both of which are incorporated herein by reference in their respective entireties. To be easily integrated into existing operating methods, it may be desirable for the automatic property measurements to closely mimic manual measurement methods. In many cases, this requires control of the temperature and pressure conditions when measurements are taken. For example, the Rheology of the drilling fluid is usually measured at 120° F. for water based fluids and 150° F. for oil based fluids.

While particular embodiments and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A fluid analysis system for determining at least one characteristic of a drilling fluid, the fluid analysis system comprising:
   a pump;
   first and second reversible fluid ports each configured, when in a first state, to intake drilling fluid into the fluid analysis system and, when in a second state, to expel drilling fluid from the fluid analysis system;
   a valve fluidly coupling the first and second reversible fluid ports to the pump, the valve being configured to control the respective states of the reversible fluid ports; and
   at least one measurement module fluidly coupled to the pump to receive drilling fluid therefrom, the at least one measurement module being configured to determine at least one characteristic of the received drilling fluid.

2. The fluid analysis system of claim 1, further comprising a first filter fluidly coupled with the first reversible fluid port and a second filter fluidly coupled with the second reversible fluid port.

3. The fluid analysis system of claim 2, wherein each of the filters includes a wire screen configured to prevent solids of a predetermined size from entering the fluid analysis system.

4. The fluid analysis system of claim 2, wherein each of the filters is configured to withstand a pressure of at least approximately 14 psi when the corresponding reversible fluid port thereof is in the first state, and a pressure of at least approximately 100 psi when the corresponding reversible fluid port thereof is in the second state.

5. The fluid analysis system of claim 1, further comprising a pneumatic device configured to introduce pressurized air into the expelled drilling fluid.

6. The fluid analysis system of claim 1, further comprising a conditioning device configured to modify at least one property of the drilling fluid prior to delivery of the fluid to the at least one measurement module.

7. The fluid analysis system of claim 6, wherein the conditioning system includes a heat exchanger configured to modify a measurement temperature of the drilling fluid.

8. The fluid analysis system of claim 6, wherein the conditioning system includes a pressurizing device configured to modify a measurement pressure of the drilling fluid.

9. The fluid analysis system of claim 1, wherein the at least one measurement module includes an enclosure configured to permit operation of the at least one measurement module in environments with flammable elements.

10. The fluid analysis system of claim 1, wherein the at least one measurement module is further configured to generate a signal indicative of the at least one characteristic of the received drilling fluid, the at least one measurement module including a communication device for transmitting the signal.

11. The fluid analysis system of claim 1, wherein the at least one measurement module includes an air injection port configured to introduce pressurized air into the drilling fluid.

12. The fluid analysis system of claim 1, wherein the at least one measurement module includes a fault detection sensor configured to detect the occurrence of a fault even and output a single indicative thereof.

13. The fluid analysis system of claim 1, wherein the valve includes a flow reversal valve selectively operable to switch a direction of flow of the drilling fluid through the first and second reversible fluid ports.

14. The fluid analysis system of claim 1, further comprising a controller operatively connected to and configured to control the valve and the pump.

15. A fluid analysis system for determining one or more characteristics of a drilling fluid, the fluid analysis system comprising:
a pump configured to move drilling fluid through the analysis system;
first and second reversible fluid ports each configured to switch between an intake and an outlet state, the reversible fluid ports being configured to intake a sample of the drilling fluid when in the intake state, and to expel the sample of drilling fluid when in the outlet state;
a first filter fluidly coupled with the first reversible fluid port;
a second filter fluidly coupled with the second reversible fluid port;
a flow reversal valve fluidly coupling the first and second reversible fluid ports to the pump, the flow reversal valve being configured to selectively change the respective states of the first and second reversible fluid ports between the intake and outlet states;
a controller operatively connected to and configured to control the flow reversal valve and the pump; and
a plurality of measurement modules fluidly coupled to the pump and the flow reversal valve, each of the measurement modules being configured to measure a respective characteristic of the drilling fluid and output a signal indicative thereof 16. A method of operating a drilling fluid analysis system, the method comprising:
drawing a sample of drilling fluid into the analysis system via a first reversible fluid port of the drilling fluid analysis system;
determining, via a measurement module of the drilling fluid analysis system, at least one characteristic of the drilling fluid sample;
generating, via the measurement module, a signal indicative of the at least one characteristic; and
reversing the first reversible fluid port from an intake state to an outlet state such that drilling fluid is expelled therefrom; and
reversing a second reversible fluid port from an outlet state to an intake state such that the second reversible fluid port draws drilling fluid into the analysis system, wherein the reversing the first reversible fluid port from the intake state to the outlet state and the reversing the second reversible fluid port from the outlet state to the intake state is achieved via a flow reversal valve of the drilling fluid analysis system, the flow reversal valve being configured to selectively change the respective states of the first and second reversible fluid ports between the intake and outlet states.

17. The method of claim 16, further comprising introducing pressurized air into the drilling fluid flowing out through the first reversible fluid port.

18. The method of claim 16, further comprising cleaning a drilling fluid flow path inside the measurement module after the determining of the at least one characteristic of the drilling fluid sample.

19. The method of claim 16, further comprising modifying at least one property of the drilling fluid sample prior to delivering the drilling fluid sample to the measurement module.

20. The method of claim 16, wherein a controller is operatively connected to and configured to control the flow reversal valve.

* * * * *